United States Patent
Uihlein

(10) Patent No.: US 9,174,022 B2
(45) Date of Patent: Nov. 3, 2015

(54) MEDICAL CATHETER INSTRUMENT

(75) Inventor: Bernhard Uihlein, Dettlingen (DE)

(73) Assignee: EPflex Feinwerktechnik GmbH, Dettingen/Erms (DE)

(*) Notice: Subject to any disclaimer, the term of this patent is extended or adjusted under 35 U.S.C. 154(b) by 520 days.

(21) Appl. No.: 13/389,545

(22) PCT Filed: May 4, 2010

(86) PCT No.: PCT/EP2010/056039
§ 371 (c)(1), (2), (4) Date: Apr. 16, 2012

(87) PCT Pub. No.: WO2011/018249
PCT Pub. Date: Feb. 17, 2011

(65) Prior Publication Data
US 2012/0190927 A1 Jul. 26, 2012

(30) Foreign Application Priority Data
Aug. 10, 2009 (DE) .................. 10 2009 037 827

(51) Int. Cl.
*A61M 25/092* (2006.01)
*A61M 25/01* (2006.01)
(Continued)

(52) U.S. Cl.
CPC .......... *A61M 25/0144* (2013.01); *A61B 1/0053* (2013.01); *A61M 25/0141* (2013.01);
(Continued)

(58) Field of Classification Search
CPC ............. A61M 2025/0063–2025/0065; A61M 2025/09133; A61M 61/0915; A61M 25/0052–25/0054; A61M 25/0133; A61M 25/0141; A61M 25/0144; A61M 25/0147; A61B 2017/003; A61B 2017/00318; A61B 1/0053; G02B 23/2476
USPC ...................... 604/528–536, 95.04
See application file for complete search history.

(56) References Cited

U.S. PATENT DOCUMENTS 5,199,950 A 4/1993 Schmitt et al.
5,381,782 A * 1/1995 DeLaRama et al. .......... 600/149
(Continued)

FOREIGN PATENT DOCUMENTS

DE 10 2007 006 185 A1 8/2008
DE 103 37 580 B4 7/2009
(Continued)

OTHER PUBLICATIONS

German-language Office Action dated Aug. 11, 2010 (Five (5) pages).
(Continued)

*Primary Examiner* — Bhisma Mehta
*Assistant Examiner* — Jenna Zhang
(74) *Attorney, Agent, or Firm* — Crowell & Moring LLP

(57) ABSTRACT

A medical catheter instrument has a shaft portion, a distal portion bendable in a controlled manner in at least one direction relative to the shaft portion, and a control element extending in an axially movable manner through the shaft portion to the distal portion. The axial movement of the control element controls a corresponding bending movement of the distal portion. The catheter instrument includes a bending assembly having at least one elongated, elastically bendable stiffening element and at least one elongated, bendable and axially length-adjustable bending element, the elements being provided in an axial sub-region of the distal portion and extending therein with an axial main component, wherein the stiffening element forms an element restoring bending movement and has a higher flexural stiffness than the bending element, and the bending element is coupled to the control element or forms part of the same.

18 Claims, 8 Drawing Sheets

(51) Int. Cl.
  *A61B 1/005* (2006.01)
  *G02B 23/24* (2006.01)
  *A61B 17/00* (2006.01)
  *A61M 25/00* (2006.01)

(52) U.S. Cl.
  CPC ....... *A61M25/0147* (2013.01); *G02B 23/2476* (2013.01); *A61B 2017/003* (2013.01); *A61B 2017/00318* (2013.01); *A61B 2017/00331* (2013.01); *A61M 25/0052* (2013.01)

(56) References Cited

U.S. PATENT DOCUMENTS

| | | | |
|---|---|---|---|
| 5,630,783 A * | 5/1997 | Steinberg | 600/158 |
| 6,450,948 B1 | 9/2002 | Matsuura et al. | |
| 6,544,215 B1 | 4/2003 | Bencini et al. | |
| 7,033,345 B2 | 4/2006 | Lee et al. | |
| 2002/0161353 A1 * | 10/2002 | Kortelling | 604/528 |
| 2002/0177766 A1 | 11/2002 | Mogul | |
| 2004/0087932 A1 * | 5/2004 | Lawrence et al. | 604/524 |
| 2007/0021737 A1 * | 1/2007 | Lee | 606/1 |
| 2007/0100235 A1 * | 5/2007 | Kennedy, II | 600/434 |
| 2007/0208364 A1 * | 9/2007 | Smith et al. | 606/191 |
| 2011/0077498 A1 * | 3/2011 | McDaniel | 600/374 |

FOREIGN PATENT DOCUMENTS

| | | |
|---|---|---|
| EP | 0 489 937 B1 | 6/1995 |
| EP | 1 484 003 A1 | 12/2004 |
| EP | 1 690 564 A1 | 8/2006 |
| WO | WO 95/31243 A1 | 11/1995 |
| WO | WO 97/01369 A1 | 1/1997 |

OTHER PUBLICATIONS

International Search Report dated Aug. 3, 2010 including English-language translation (Six (6) pages).
International Preliminary Report on Patentability dated Feb. 23, 2012 (Fourteen (14) pages).

* cited by examiner

MEDICAL CATHETER INSTRUMENT

BACKGROUND AND SUMMARY OF THE INVENTION

The invention relates to a medical catheter instrument comprising a shaft portion, a distal portion that can be bent in a controlled manner in at least one direction relative to the shaft portion, and at least one control element that extends in an axially moveable manner through the shaft portion to the distal portion; and that the axial movement of the control element controls a corresponding bending movement of the distal portion.

Medical catheter instruments of this kind are known in various designs. Thus, the patent specification U.S. Pat. No. 7,033,345 B2 discloses a catheter instrument with a control element that is formed by a tension wire, which extends from a grip region of the catheter through the shaft portion and the distal portion inside an associated tension wire lumen as far as the front end of the distal portion, where said tension wire is fastened. A more or less central hollow channel serves as the working channel. In an additional lumen the distal portion has a rubber element with a rectangular cross section. This rubber element acts as the stiffening element, which is supposed to bring about the resetting of the distal portion into its linear starting position from its bent position, when the restoring movement is released by relaxing the tension wire.

The patent specification EP 0 489 937 B1 discloses a medical catheter instrument with two tension cable pieces, which serve as the control element for controlling an active bending movement of the distal portion in a plane of the bending movement. These two pieces of the tension cables are arranged opposite each other with respect to a longitudinally central working/hollow channel of the catheter. In this case the tension wires run directly in a respective lumen of solid material inside the distal portion, whereas inside the shaft portion the tension wires run in a sleeve that increases the flexural rigidity and that in turn is inserted into a corresponding lumen of solid material. In the plane that extends perpendicular to the plane of the bending movement, strips having a rectangular cross section are incorporated into the distal portion. Said strips are supposed to stabilize the distal portion and to counteract the said distal portion's deflections transversely to the plane of the bending movement. The tension cable pieces are implemented as sections of a common continuous tension cable comprising a connecting piece that is fastened at a front end cap of the distal portion.

The patent specification DE 103 37 580 B4 discloses a catheter that is provided with a control element that is designed to transmit both pull and push forces, so that the result is a deflectability of the distal portion of the catheter in two opposite directions with the use of only this one control element.

Additional medical catheter instruments of the type mentioned in the introductory part are disclosed in the Offenlegungsschrift [published patent application] WO 97/01369 A1 and WO 95/31243 A1.

The engineering object of the present invention is to provide a medical catheter instrument of the type mentioned in the introductory part that enables a deflectability of the distal portion with a high degree of functional reliability, a high degree of flexibility when in use and/or at a comparatively low production cost.

The invention achieves this object by providing a medical catheter instrument comprising a shaft portion, a distal portion that can be bent in a controlled manner in at least one direction relative to the shaft portion, and at least one control element that extends in an axially moveable manner through the shaft portion to the distal portion. The axial movement of the control element controls a corresponding bending movement of the distal portion. At least one bending assembly comprises at least one elongated, elastically flexible stiffening element and at least one elongated, flexible and axially length-variable bending element. The stiffening element and the bending element are both provided in at least one axial subregion of the distal portion and extend therein with an axial main component, wherein the stiffening element forms a bending movement restoring element, which has a higher flexural rigidity than the at least one bending element. The bending element is coupled to the at least one control element or forms a part of the control element.

This catheter instrument contains one or more bending assemblies that comprise at least one elongated, elastically flexible stiffening element and at least one elongated, flexible and axially length-variable bending element. The stiffening element and the bending element are both provided in at least one axial subregion of the distal portion and extend therein with an axial main component—that is, totally or in any case predominantly in the axial direction. At the same time the stiffening element forms an element that restores the bending movement and has a higher flexural rigidity than the bending element. The bending element is coupled to the control element, which exhibits an axial movement that controls the corresponding bending movement of the distal portion, or forms a part of the control element.

The stiffening element and the bending element can be introduced in each case as an independent element or rather component into the respective axial subregion of the distal portion or can be formed integrally as a part of a solid material of the distal portion and can be designed in an optimally adaptable way for its functions relating to restoring the stiffness and/or actively generating the bending movement, so that there is no need to design any other material of the catheter instrument in this region—typically a solid material, provided with one or more lumens, or a coaxial tube unit—to fulfill these functions. As a result, this feature makes it possible, if desired, to use, for example, a very pliable solid material for the basic structure of the distal catheter portion that does not have to act in either a stiffening or flexion determining manner. Rather the restoring rigidity is guaranteed by the stiffening element that is incorporated, for example, as a separate element into the pliable solid material or is formed by a solid material zone that exhibits a higher flexural rigidity. The bending element defines together with the control element the active bending movement. The bending element can enable in interaction with the stiffening element an enhanced functionality in terms of the active bending movement as compared, for example, to the conventional bending arrangements with a tension wire control element that acts only on a distal end cap region of a homogenous solid material of the distal portion.

In a further development of the invention the stiffening element extends from the distal portion into the shaft portion. In this way the stiffening element can contribute to providing the shaft portion with a flexural rigidity that is typically necessary for the shaft portion and that is significantly higher than the flexural rigidity of the actively flexible distal portion.

In a further development of the invention the control element is formed by a tension wire that is guided through a hollow channel of the bending element and is coupled to a distal end region of the bending element by means of, for example, a thickened head piece. A tension wire that is suitable for the present invention includes any type of wire that is used in the customary way for this purpose. For the sake of simplicity the term tension wire in the present invention shall also include tension cables of any kind.

In an additional embodiment the bending element has two hollow channels, through which the tension wire is guided in one piece so as to form a return bend at the distal end region of the bending element. This simple design feature makes it possible to produce the bending movement by a synchronous pulling at the two proximal sections of the tension wire, so that the return bend transmits the pulling force to the bending element.

In a further development of the invention the bending element is implemented by an elastically compressible helical spring element or hollow rod element or an elastically compressible solid material zone of the distal portion. In the specific case the bending element can be formed, for example, by a helical spring having windings, which are axially spaced apart from each other in the unstressed state, or by a relatively flexurally pliable solid material zone of the distal portion.

In a further development of the invention the stiffening element is formed by an elastically tensible helical spring element or rod element or an elastically tensible solid material zone of the distal portion. In the specific case the stiffening element can be formed, for example, by a helical spring having windings, which are axially spaced apart from each other in the unstressed state, or a relatively flexurally pliable solid material zone of the distal portion.

In a further development of the invention the stiffening element and the bending element can be arranged opposite each other relative to a longitudinally central axis of the distal portion. This feature allows at least one bending movement in the plane of the stiffening element and the bending element in the one and/or the other bending direction, depending on whether the bending element is subject to a push or pull force by means of the control element.

In a further development of the invention the bending assembly comprises at least two bending elements, which are arranged opposite each other in the plane of the bending movement, and at least two stiffening elements, which are arranged side by side in a plane transversely to the plane of the bending movement. This feature allows the distal portion to be bent in both directions in the plane of the bending movement, even if only control elements, which work by means of pull forces and not by means of push forces, are used exclusively.

In a further development of the invention the distal portion of the catheter is made of a solid material or consists of two coaxial tubular elements. In this case the bending assembly is provided in the solid material or in the annular space between the coaxial tubular elements. If the bending element and the stiffening element are designed as independent elements, which satisfy the stiffening function and/or the bending actuator function, then the solid material and/or the coaxial tubular elements do not have to be designed to fulfill these functions. They need only be selected in such a way that they do not inhibit these functions of the bending element and the stiffening element. As an alternative, the bending element and/or the stiffening element can be formed by a corresponding zone of solid material, which in this case is constructed of a plurality of materials in the form of multiple zones.

In a further development of the invention the distal portion of the catheter has a central axial working channel and/or one or more off-centered axial working channels. The working channel(s) can be used, for example, for the customary catheter functions, such as for conveying a fluid or gas or for operating a functional element that is needed on the distal end, like a mirror, a knife, scissors, a sensor, etc. For this purpose the respective working channel can also extend preferably in a continuous manner through the shaft portion.

In the design of this aspect the distal portion is made of a solid material surrounding the central axial working channel with a non-uniform thickness. In this case a correspondingly flexurally rigid solid material zone, which lies in a region in which the solid material has negligible thickness, acts as the stiffening element. In addition, the tubular solid material can be easily manufactured, for example, by an extrusion process using at least two materials of different flexural rigidity. In an additional design the solid material also has a zone that acts as a bending element and that lies in a region of greater thickness. Even for this design the solid material can be fabricated, for example, as a suitably extruded tubular component.

In a further development of the invention the catheter instrument comprises a plurality of bending assemblies, each of which has at least one stiffening element and at least one bending element of the aforementioned type. In this case the bending assemblies are provided in different axial subregions of the distal portion; and at least two bending assemblies have bending movement planes that do not extend parallel to each other. This feature allows the distal portion to be bent in a plurality of non-parallel planes of the bending movement.

In a further development of the invention the distal portion of the catheter comprises at least one light guide element and, coupled thereto, a luminous ring. In this case the light guide element is accommodated in an axially extending manner in a working channel of the distal portion. At the same time the luminous ring can serve as a light guide on the distal front end of the catheter.

In a further development of the invention the distal portion of the catheter comprises a distal end piece, which can be moved in an axially elastic manner. This distal end piece is connected to at least one guide pin, which can be guided in an axial hollow channel of the distal portion in such a way that it can be moved in an axially elastic manner. In this structurally simple way the distal portion of the catheter is flexible in an axial elastic manner on its distal end, so that the risk of injuring, for example, a body tissue in the course of inserting the catheter instrument can be eliminated.

BRIEF DESCRIPTION OF THE DRAWINGS

Advantageous embodiments of the invention are shown in the drawings and are described below. Referring to the drawings.

DETAILED DESCRIPTION OF THE DRAWINGS

Figure 1:
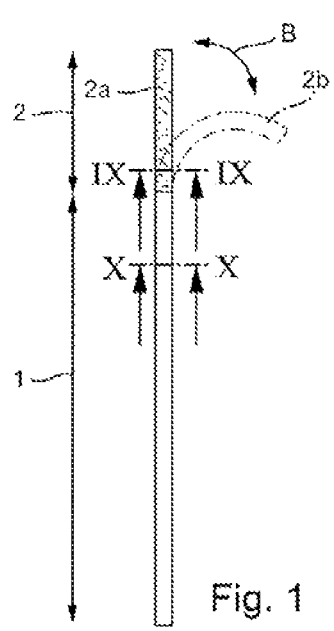
FIG. 1 is a side view in schematic form of that part of a medical catheter instrument that is of interest here and that has a flexible distal portion.

FIG. 1 shows a tubular part of a medical catheter instrument only in a schematic form. The tubular part includes a shaft portion 1 and a flexible portion 2. The instrument's handle part, which is proximally connected in a conventional way to the shaft portion 1, has been omitted for the sake of simplicity. The distal portion 2 can be bent, as symbolized with a deflection arrow B, in a controlled manner between a first end position 2a, which is linear in the illustrated example, and a maximally bent second end position 2b, which is indicated by the dashed line.

Figure 2:
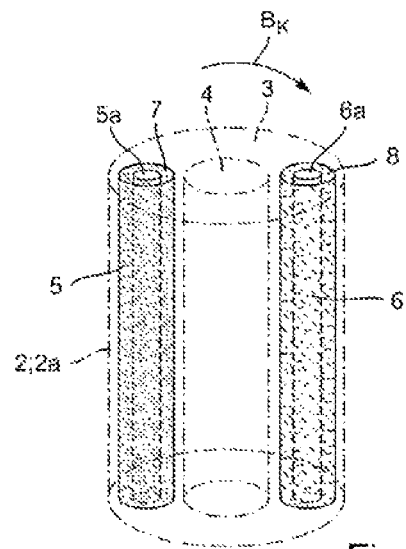
FIG. 2 is a perspective view in schematic form of an axial subregion of the flexible distal portion of a catheter that conforms to the type from FIG. 1 and has a bending assembly comprising a bending element and a stiffening element.

FIG. 2 is a perspective view in schematic form of the distal portion 2 in its linear end position 2a for a specific, advantageous embodiment. It is very clear from the figure that a tubular solid material 3 has a longitudinally central lumen 4, which acts as an axial working channel of the catheter, and also a stiffening element 5 and a bending element 6, both of which are incorporated in an axially extending manner in said tubular solid material.

Figure 3:
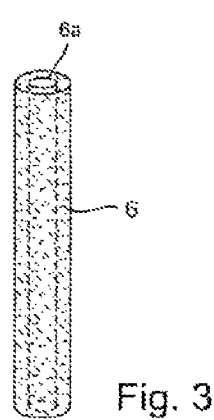
FIG. 3 is a perspective view of the bending element from FIG. 2.

The bending element 6 is shown as a separate component in FIG. 3 and has the form of a hollow rod with a central hollow channel 6a. Similarly the stiffening element 5 is formed as a rod-shaped element with a longitudinally central hollow channel 5a. The bending element 6 is made of an elastic material in such a way that it is elastically flexible and, therefore, in particular, also elastically length-variable in its axial elongation; in particular, it can be contracted. The stiffening element 5 exhibits a higher flexural rigidity than the bending element 6 and the solid material 3. The stiffening element 5 and the bending element 6 are in each case inserted into a corresponding axial hollow channel 7, 8 of the solid material 3 in such a way that they are opposite each other with respect to the longitudinally central axis of the distal portion 2 of the catheter.

The stiffening element 5 and the bending element 6 can be implemented, for example, by means of suitable tubular pieces with different elastic materials. In this case the tube material for the bending tube 6 is significantly more pliable than that for the stiffening tube 5, so that the bending element 6 is not only flexible, but also axially contractible to the degree required, whereas the stiffening element 5 is a more pressure stable element that cannot be compressed or in any case is less compressible in the axial direction. The solid material 3 of the catheter tube can be even more pliable than that of the bending element 6 and can form in any case a multi-lumen tube with at least three axial hollow channels 4, 7, 8 in the distal portion 2, as illustrated in FIG. 2.

The bending assembly that is implemented with the stiffening element 5 and the bending element 6 enables an active bending of the distal portion from its linear starting position, according to FIG. 2, into a bent position, as symbolized with the deflection arrow BK. In order to produce a controlled bending of the distal portion, a control element is provided in the form of a tension wire 9 (shown in FIG. 4). One end of the tension wire is provided with a thickened head piece 9a. In the assembled state shown in FIG. 5, the tension wire 9 extends through the hollow channel 6a of the bending element 6, so that the head piece 9a of said tension wire extends distally beyond the bending element 6 and rests axially against said bending element in the direction of pull. It is self-evident that, as an alternative to this head piece design, it is also possible to implement the desired tensible coupling of the distal end of the tension wire to the distal end of the bending element in other conventional ways, for example by adhesive cementing, welding or soldering. In the conventional design, which is not depicted in detail for this reason, the tension wire 9 extends in the proximal direction through the shaft portion 1 to a handle/actuating portion of the catheter instrument. At the handle/actuating portion, a user can apply tension to the tension wire, as symbolized by an associated tension force arrow F in FIG. 6. The tension force that is applied is transferred from the tension wire 9 over its head piece 9a to the bending element 6.

Figure 6:
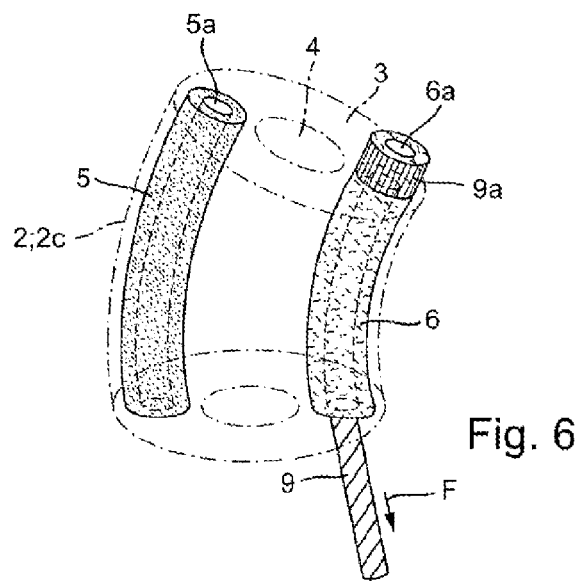
FIG. 6 is a view from FIG. 5 with the actively bent distal portion.

Since the bending element 6 can be contracted in an axially elastic manner and the stiffening element 5 has a flexural rigidity that is higher than that of the bending element 6, the effect of the pulling force on the bending element 6 results in an axial shortening of this bending element, whereas the axial length of the stiffening element 5 does not decrease or in any event decreases less than the length of the bending element 6 or even increases. The overall effect of this phenomenon is a deflecting bending of the bending element 6, of the flexurally elastic stiffening element 5 and the flexible solid material 3 into a curved position 2c in the direction of the side of the bending element 6, as shown in FIG. 6. At the same time the bending position between the two end positions 2a, 2b from FIG. 1 is variably adjusted—that is, continuously—by suitably operating the tension wire 9.

If the tension force applied to the tension wire 9 is relaxed again, then the stiffening element 5 pushes the distal portion 2 of the catheter back again into its starting position owing to the flexural rigidity of said stiffening element. In the illustrated example, this starting position is, according to FIG. 5, the linear starting position 2a, which at the same time represents the unstressed starting position of the stiffening element 5. In alternative designs the unstressed starting position can also be a curved position of the distal portion 2.

Figure 7:
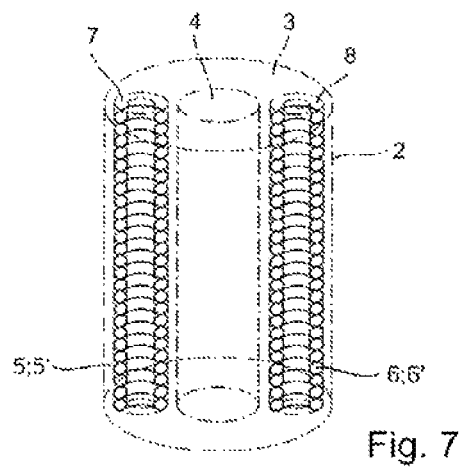
FIG. 7 is a view corresponding to FIG. 2 for a variant with helical springs as the bending and stiffening elements.

FIG. 7 shows a catheter variant with a bending assembly comprising the stiffening element 5 and the bending 6 that are implemented in each case by a helical spring 5', 6'. In the unstressed starting state the windings of the helical spring 5' of the stiffening element rest against each other with touching contact. That is, the helical spring 5' and correspondingly the stiffening element 5 are not axially contractible and are, therefore, stable to pressure, but elastically tensible and are, therefore, flexible and stretchable. In contrast, the adjacent windings of the helical spring 6' of the bending element are spaced axially apart, so that the resulting bending element 6 is not only flexible and stretchable, but is also elastically compressible and is, therefore, axially contractible—states that are required for the bending element function operating under tension. In FIG. 7 and all other figures, like reference numerals and characters are used not only for identical, but also for functionally equivalent components for the sake of a better understanding. The interior of the respective helical springs 5', 6' forms the corresponding hollow channel 5a, 6a of the stiffening element 5' or the bending element 6'.

Figure 8:
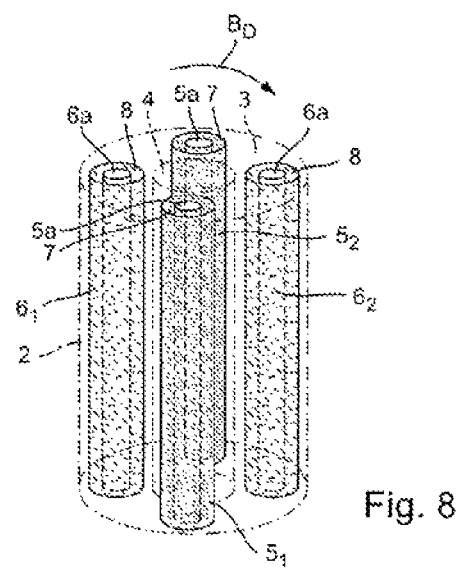
FIG. 8 is a view corresponding to FIG. 2 for a variant with a bending assembly comprising a pair of opposing bending and stiffening elements.

FIG. 8 shows a catheter variant, wherein the distal portion 2 can be bent, starting from the illustrated linear, unstressed starting position, into both opposite directions of an associated plane of flexure, as symbolized by a deflection arrow $B_D$. In this case the bending assembly of the distal portion 2 has two bending elements $6_1$, $6_2$ and two stiffening elements $5_1$, $5_2$. The two bending elements $6_1$, $6_2$, which extend axially and lie opposite each other relative to the longitudinally central axis of the distal portion 2 of the catheter, are inserted into the corresponding hollow channels of the solid material 3. Similarly the two stiffening elements $5_1$, $5_2$, which extend axially and lie opposite each other relative to the longitudinally central axis of the distal portion 2 of the catheter, are inserted into the corresponding hollow channels of the solid material 3, so that said stiffening elements are offset relative to the bending elements $6_1$, $6_2$ by 90° in the circumferential direction of the solid material 3. The bending elements $6_1$, $6_2$ and the stiffening elements $5_1$, $5_2$ can be of any one of the design types described above with reference to FIGS. 1 to 7.

Figure 4:
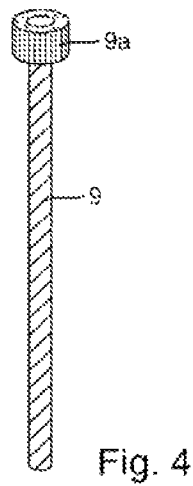
FIG. 4 is a perspective view of a tension wire, which can be used as the bending movement control element for the catheter from FIGS. 1 and 2.
Figure 5:
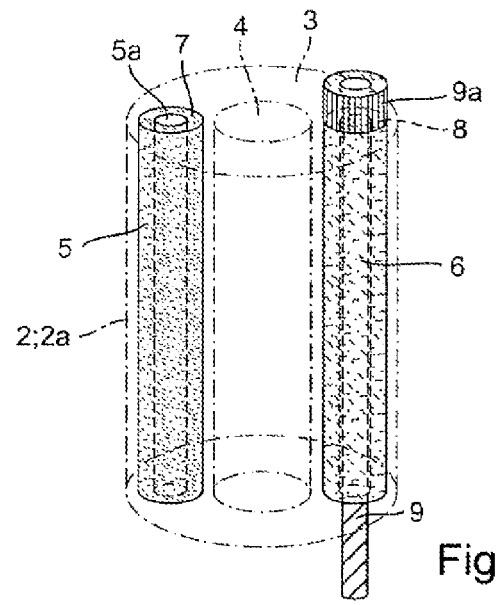
FIG. 5 is a view from FIG. 2 with the tension wire from FIG. 4 in the installed state.

Each of the two bending elements $6_1$, $6_2$ is assigned a control element that is similar to the tension wire 9 from FIG. 4. When tension is applied to the tension wire, which is assigned to the bending element $6_2$, shown on the right in FIG. 8, this tension wire pushes against this bending element $6_2$, which contracts as a result.

Together with the pressure stable stiffening elements $5_1$, $5_2$, the effect is a deflection of the distal portion 2 to the side of the pressure loaded bending element $6_2$—that is, to the right in FIG. 8. Of course, no pull force is exerted on the other bending element $6_1$. If inversely pressure is applied to the bending element $6_1$, which is located on the left in FIG. 8, and if the bending element $6_2$, which is located on the right in FIG. 8, is relieved of pressure, then the distal portion 2 bends from its linear position in FIG. 8 to this side—that is, to the left in FIG. 8.

Consequently the plane, in which the two bending elements $6_1$, $6_2$ lie, forms a plane of flexure, in which the distal portion 2 of the catheter can deflect from its linear starting position by choice into the one or the other of its two opposite bending directions. The two stiffening elements $5_1$, $5_2$ lie in a longitudinal plane of the distal catheter portion 2 that is, in particular, perpendicular in the illustrated example and does not lie parallel to the plane of flexure. These two stiffening elements act as the elements that define the flexural rigidity and have the effect of resetting the bent distal portion 2 of the catheter into its linear starting position, when the tension force that controls the bending is relaxed at the respective tension wire.

FIGS. 9 to 15 are cross sectional views in a schematic form of a plurality of catheter variants with respect to the design of the distal catheter portion 2 and the shaft portion 1.

Figure 9:
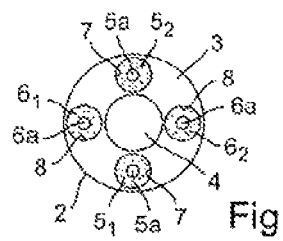
FIG. 9 is a cross sectional view of the distal portion along a line IX-IX from FIG. 1 for the variant from FIG. 8.

In particular, FIG. 9 is a cross sectional view along a line IX-IX from FIG. 1 in the distal catheter portion 2 for the catheter variant from FIG. 8. It shows very clearly the solid material 3, which forms the multi-lumen tube, the central working channel 4, the two stiffening elements $5_1$ and $5_2$, as well as the two bending elements $6_1$ and $6_2$.

Figure 10:
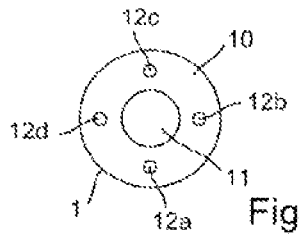
FIG. 10 is a cross sectional view of the shaft portion along a line X-X of the catheter variant from FIG. 8.

FIG. 10 is a cross sectional view along a line X-X in the shaft portion 1 from FIG. 1 for implementing a shaft made of a multi-lumen tube solid material 10 with a longitudinally central hollow/working channel 11 and four hollow/working channels 12a, 12b, 12c, 12d, which are arranged in an eccentric manner so as to be offset by 90°. The central working channel 11 corresponds to the central working channel 4 of the distal portion—that is, forms a corresponding working channel that extends through the shaft portion 1 and the distal portion 2, whereas each of the eccentric working channels 12a to 12d corresponds to one of the hollow channels 5a, 6a, which are provided in the two stiffening elements $5_1$, $5_2$ and the two bending elements $6_1$, $6_2$. In this case the hollow channels 12b, 12d, which are assigned to the bending elements $6_1$, $6_2$, serve for the passage of the respective tension wire, whereas the two other hollow channels 12a, 12c can be used elsewhere. The solid material 10 of the shaft portion 1 has preferably a higher rigidity than the solid material 3 of the distal portion 2.

Figure 11:
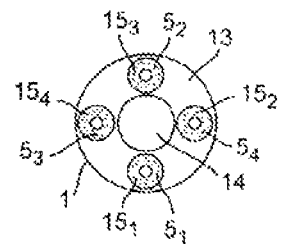
FIG. 11 is a view corresponding to FIG. 10 for a variant with additional stiffening elements in the shaft portion.

FIG. 11 shows a variant with the shaft portion 1 that is formed by a multi-lumen tube solid material 13, in which a central hollow/working channel 14 and four hollow channels $15_1$, $15_2$, $15_3$, $15_4$, which are arranged in an eccentric manner equidistant in the circumferential direction, are incorporated. The four hollow channels receive one stiffening element $5_1$, $5_2$, $5_3$, $5_4$ each. The stiffening elements, which lie opposite the one pair $5_1$, $5_2$, may involve the stiffening elements of the variant from FIG. 8, where they extend from the distal portion 2 into the shaft portion 1 and, in so doing, extend over a part or the entire length of the shaft portion 1 and contribute to its additional rigidity. The two other stiffening elements $5_3$ and $5_4$ extend only in the shaft portion 1 and connected to them in the distal portion are the two bending elements $6_1$, $6_2$. The hollow channels 7, 8, $15_1$ to $15_4$ for receiving the bending elements $6_1$, $6_2$ and the stiffening elements $5_1$ to $5_4$ can extend—for example, with the same diameter throughout—through the shaft portion 1 and the distal portion 2. In this variant the solid material 13 of the shaft portion 1 can be, if desired, identical to the solid material 3 of the distal portion 2. Then the higher flexural rigidity of the shaft portion 1 is guaranteed by the additional stiffening elements $15_2$, $15_4$.

Figure 12:
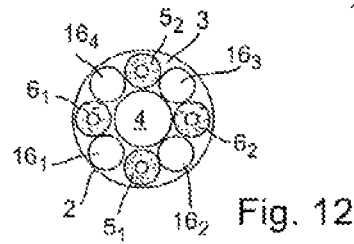
FIG. 12 is a view corresponding to FIG. 9 for a variant with additional off-centered working channels.
Figure 13:
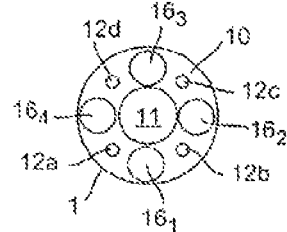
FIG. 13 is a view corresponding to FIG. 10 for the variant from FIG. 12.

FIG. 12 shows a variant with four additional working/hollow channels $16_1$, $16_2$, $16_3$, $16_4$, which are incorporated, based on the variant of FIGS. 8 and 9, into the multi-lumen tube material 3 of the distal portion 2. Working on this basis, FIG. 13 shows a variant with these additional working/hollow channels $16_1$ to $16_4$, which also extend through the shaft portion 1. For this reason the corresponding multi-lumen tube solid material 10 from FIG. 10 is provided with these four additional lumens $16_1$ to $16_4$. The four additional working/ hollow channels $16_1$ to $16_4$ can be used for additional catheter functions, for example for the passage of light fibers, laser fibers, electrical lines for signal conditioning or for carrying out measurements or for the passage of fluids or gases.

Figure 14:
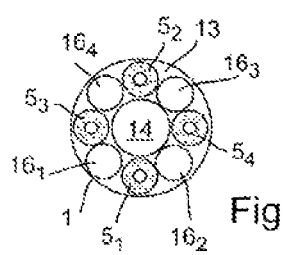
FIG. 14 is a view corresponding to FIG. 11 for the variant from FIG. 12.

FIG. 14 shows a variant with the four additional working/hollow channels $16_1$ to $16_4$, which are incorporated, in addition to the hollow channels $15_1$ to $15_4$ for receiving the stiffening elements $5_1$ to $5_4$, into the multi-volume tube solid material 13 of the shaft portion 1 of the variant from FIG. 11.

Figure 15:
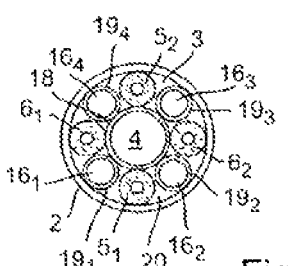
FIG. 15 is a view corresponding to FIG. 12 for a tube variant.

FIG. 15 shows a variant that corresponds in its function to the variant from FIG. 12. In this case the illustrated distal portion 2 has, instead of a multi-lumen tube solid material, two coaxial tube elements 17, 18, in particular an external tube 17 and an internal tube 18. The internal tube 18 defines in its interior the central working/hollow channel 4, whereas the external tube 17 defines together with the internal tube 18 an annular space 20, into which the two bending elements $6_1$, $6_2$ and the two stiffening elements $5_1$, $5_2$ as well as the four tube pieces $19_1$, $19_2$, $19_3$, $19_4$ are inserted, and they in turn define the four eccentric working/hollow channels $16_1$ to $16_4$. Compared to the multi-lumen tube solid material variant, this catheter tube variant has the advantage that the tube materials for the individual tube elements or tube pieces can be chosen in a variable manner and optimally adapted, as desired, to the application, and the cost of production can be reduced compared to a comparable multi-lumen tube solid material.

Figure 16:
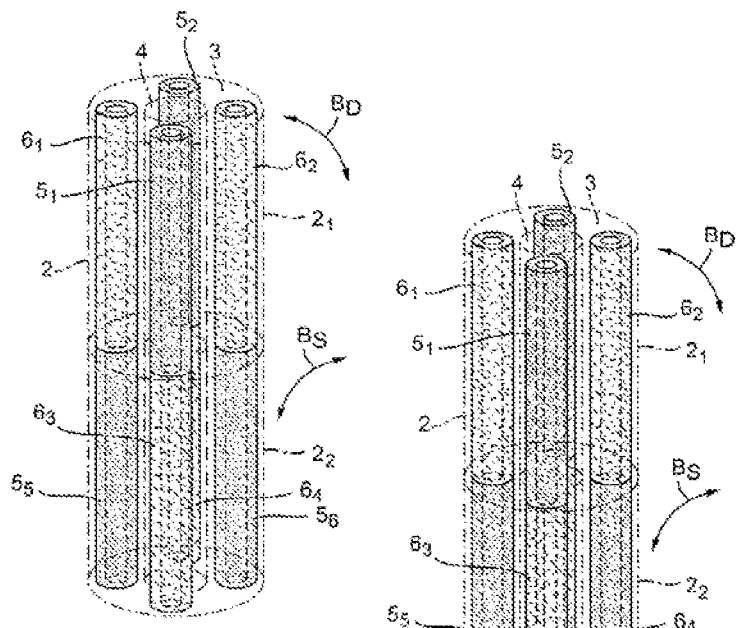
FIG. 16 is a perspective view of the distal portion of a catheter variant with flexibility in two non-parallel planes.

FIG. 16 shows a catheter variant, in which the flexible distal portion 2 has a plurality of bending assemblies in different axial subregions, in particular a first bending assembly with two opposite bending elements $6_1$, $6_2$ and two opposite stiffening elements $5_1$, $5_2$ corresponding to the bending assembly from FIG. 8 in a first subregion $2_1$ and a second bending assembly with two opposite bending elements $6_3$, $6_4$ and two opposite stiffening elements $5_5$, $5_6$ also along the line of the bending assembly from FIG. 8 in a second subregion $2_2$, which is connected proximally to the first subregion. In this case the second bending assembly is rotated by 90° relative to the first bending assembly—that is, connected in the axial direction to the two stiffening elements $5_5$, $5_6$ of the second bending assembly are the two bending elements $6_1$, $6_2$ of the first bending assembly, whereas connected to the two bending elements $6_3$, $6_4$ of the second bending assembly are the stiffening elements $5_1$, $5_2$ of the first bending assembly.

The result is that in the drawing from FIG. 16 the flexure plane of the first bending assembly lies in the drawing plane, and the distal portion in this subregion $2_1$ can be bent in a controlled manner in both directions in this plane of flexure, starting from the illustrated linear starting position (see the deflection arrow $B_D$ according to FIG. 8), whereas the second bending assembly at the distal portion's proximal subregion can bend in a controlled manner this proximal subregion $2_2$ of the distal portion 2 from its illustrated linear starting portion in both opposite direction in a flexure plane perpendicular to the drawing plane, a state that is symbolized by a deflection arrow $B_S$. In order to receive the bending elements $6_1$ to $6_4$ and the stiffening elements $5_1$, $5_2$, $5_5$, $5_6$, four axial hollow channels are incorporated correspondingly into the associated solid material 3 of the multi-lumen tube in such a way that the hollow channels extend through the two subregions $2_1$, $2_2$ of the distal portion 2. Each bending element $6_1$ to $6_4$ of each of the two bending assemblies is assigned in turn, as explained above with reference to FIG. 8, a control element, for example in the form of a tension wire. In this context the tension wires (not explicitly shown in FIG. 16) for the two bending elements $6_1$, $6_2$ of the front bending assembly extend through the hollow channels of these bending elements $6_1$, $6_2$ and through the hollow channels of the proximally connected stiffening elements $5_5$, $5_6$ of the rear bending assembly.

Consequently in this catheter variant the distal portion 2 can be bent in a controlled manner into two non-parallel planes of flexure, in this case, in particular, two orthogonal planes of flexure, at any rate in opposite directions, that is, starting from its linear starting position from FIG. 16 to the left and right as well as to the front and rear. The combination of these two non-parallel bending movements—in this case, in particular, orthogonal bending movements—allows the distal portion 2 in this variant to be bent in a controlled manner in any desired direction. Once again all of the types described with respect to the above exemplary embodiments can be applied to the bending element $6_1$ to $6_4$ and the stiffening elements $5_1$, $5_2$, $5_5$, $5_6$. It is self-evident that, as an alternative, the two bending assemblies can also be provided with axial spacing and/or that the distal portion 2 can have one or more additional bending assemblies in other axial subregions.

Figure 17:
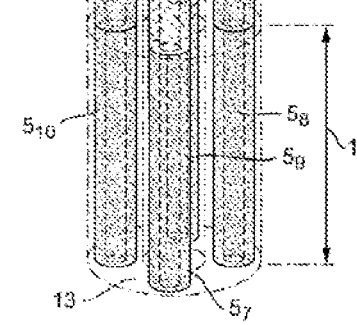
FIG. 17 is a view corresponding to FIG. 16, showing additionally a part of the shaft portion that rests against the distal portion.

FIG. 17 shows the distal portion 2, which is provided, according to FIG. 16, with the two bending assemblies and is coupled to the shaft portion 1, which in this case is implemented according to the variant from FIG. 11. That is, it is made of the multi-lumen tube solid material 13 with the four hollow channels $15_1$ to $15_4$ for receiving one stiffening element each. For this purpose four individual stiffening elements $5_7$, $5_8$, $5_9$, $5_{10}$ may be incorporated, as shown, into these hollow spaces $15_1$ to $15_4$. As an alternative, the stiffening elements $5_5$, $5_6$ of the rear bending assembly of the distal portion 2 may extend in one piece into the shaft portion 1 and form there the corresponding two opposite stiffening elements. The multi-lumen tube solid material 13 of the shaft port 1 can also be, if desired, the multi-lumen tube solid material 3 of the distal portion. That is, in this case the entire catheter tube, composed of the shaft portion 1 and the distal portion 2, comprises a uniformly continuous multi-lumen tube solid material. In order to receive the bending elements $6_1$ to $6_4$ and the stiffening elements $5_1$, $5_2$, $5_5$ to $5_{10}$, four hollow channels, which extend axially through the shaft portion 1 and the distal portion 2, may be incorporated in this solid material of the multi-lumen tube in such a way that said four hollow channels are offset by 90° in the circumferential direction.

Figure 18:
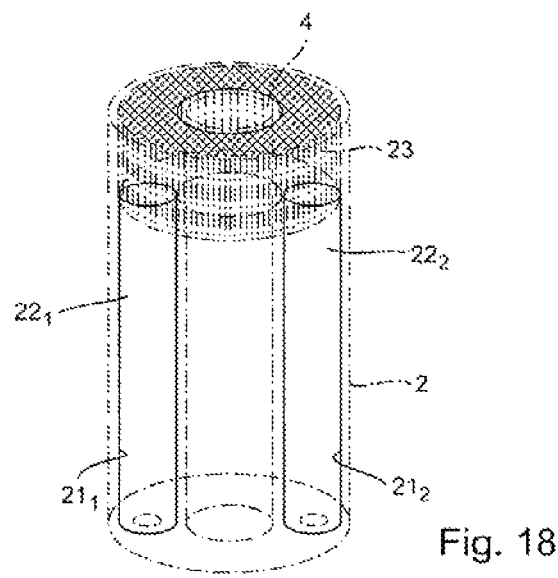
FIG. 18 is a perspective view in schematic form of a front end region of a catheter variant with a distal illuminating element.
Figure 19:
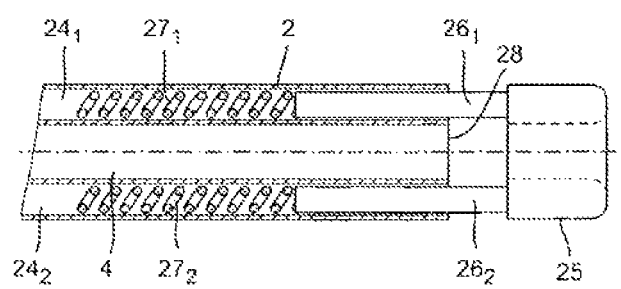
FIG. 19 is a longitudinal sectional view of the distal end region of a catheter variant with an end piece that is held in an axially elastic manner.

FIGS. 18 and 19 illustrate catheter variants exhibiting specific possibilities for the use of distally end-sided working/hollow channels, which are present in the distal portion 2, for example, in the form of the stiffening element hollow channel(s) $5a$ in the variant from FIGS. 5 to 11, 16 and 17 and/or in the form of the additional working/hollow channels $16_1$ to $16_4$ in the variants of FIGS. 12 to 15.

In the variant from FIG. 18, two axial hollow channels $21_1$, $21_2$ of the distal portion 2 are used to conduct one light guide $22_1$, $22_2$ each. Both of these light guides terminate distally at a luminous ring 23, which acts as the illuminating element at the distal end of the catheter. The light guides $22_1$, $22_2$ serve to illuminate the luminous ring 23, which makes it possible to provide a uniformly diffuse illumination at the distal end of the catheter.

The catheter variant from FIG. 19 uses eccentric axial hollow channels $24_1$, $24_2$ for an axially resilient mounting of a distal end piece or rather head piece 25 of the catheter. For this purpose the head piece 25 has two or more axial guide pins $26_1$, $26_2$, each of which projects into one of the associated hollow channels $24_1$, $24_2$. One compressible helical spring $27_1$, $27_2$ is inserted into each of the hollow channels $24_1$, $24_2$, and the proximal end of these helical springs is properly supported in a conventional way (not shown in detail). This feature allows the head piece 25 to be arranged in such a way that it can be moved in an axially elastic manner and/or gives way with respect to a distal end 28 of the catheter tube. This variant is advantageous, for instance, for applications, in which the distal end of the catheter is always supposed to rest close to a vessel wall, even if this wall is moved or is elastic.

FIGS. 20 to 25 illustrate catheter variants, in which the distal portion is formed by a tubular solid material that simultaneously provides the bending element.

Figure 20:
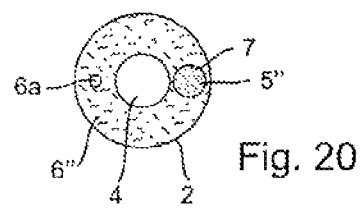
FIG. 20 is a view corresponding to FIG. 9 for a variant with a solid material zone as the bending element.
Figure 21:
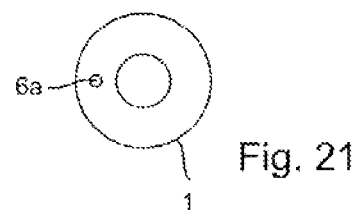
FIG. 21 is a view corresponding to FIG. 10 for the variant from FIG. 20.

Hence, in the variant from FIGS. 20 and 21 the entire circular cross section of the tubular distal portion 2 consists of a solid material, which acts as the corresponding bending element 6" and into which is incorporated the hollow channel 6a, which is provided for the passage of the associated tension wire, and the axial hollow channel 7, which receives, as in the exemplary embodiment from FIG. 2, a rod-shaped stiffening element 5", which in this example, is designed totally solid as a separate component or as, for example, an extruded integral part of the solid material. The tension wire, which is guided through the hollow channel 6a, is coupled to the distal end of the solid material bending element 6" in a manner that is described with respect to the above examples. The shaft portion 1 is formed by a tubular solid material, into which only the hollow channel (6a) for the passage of the tension wire is incorporated.

The bending properties of the variant shown in FIGS. 20 and 21 correspond to those of the variant described above with reference to FIGS. 2 to 6. Pulling on the tension wire causes the solid material bending region 6" to contract in its region depicted on the left in FIG. 20, so that the distal portion 2 bends towards the side depicted on the left in FIG. 20, because the stiffening element 5" remains axially more stable in length.

Figure 22:
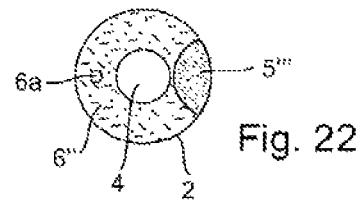
FIG. 22 is a view corresponding to FIG. 20 for a variant with a solid material zone as the stiffening element.

FIG. 22 illustrates a variant, in which the bending element is provided, as in the example from FIGS. 20 and 21, by a tubular solid material 6", which forms the distal portion 2. In this variant the stiffening element is also formed by a corresponding zone 5''' of the entire annular solid material. In other words, in this exemplary embodiment the annular solid material cross section of the distal portion 2 is divided into a partial cross section that forms the bending element 6" and into a partial cross section that forms the stiffening element 5''', so that the bending element 6" occupies the bulk of the cross section and the stiffening element 5''' is constrained to an external subzone with a significantly smaller cross sectional area, as shown in FIG. 22. In this example the shaft portion corresponds to that of the variant according to FIGS. 20 and 21. In the catheter variant from FIG. 22, the entire distal portion 2 can be manufactured advantageously by means of an extrusion process, because a flexurally more pliable material is used for the partial cross section 6" of the bending element and a flexurally more rigid material is used for the partial cross section 5''' of the stiffening element. Moreover, the bending properties of the catheter variant from FIG. 22 correspond to those of the catheter variant from FIGS. 20 and 21.

Figure 23:
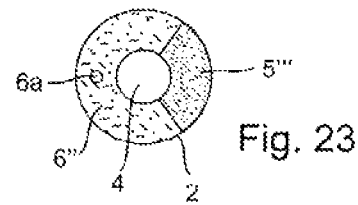
FIG. 23 is a view corresponding to FIG. 22 for a modified variant solid material zone of the stiffening element.

FIG. 23 shows a modification of the catheter variant from FIG. 22 to the effect that the partial cross section 5' of the stiffening element is designed in the form of a ring segment. In this case the solid material zone 5''' of the stiffening element extends over a circumferential angle of, for example, between 90° and 140°, whereas the solid material zone 6" of the bending element occupies the remaining, larger partial cross section. Once again the variant from FIG. 23 corresponds in its bending properties to the variants from FIGS. 20 to 22. The larger the total cross sectional share of the solid material zone 5''' of the stiffening element is selected, the less flexurally rigid the associated material can be chosen and/or the higher is its flexural rigidity.

Figure 24:
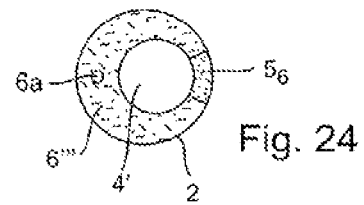
FIG. 24 is a view corresponding to FIG. 23 for a variant with an off-set central working channel.
Figure 25:
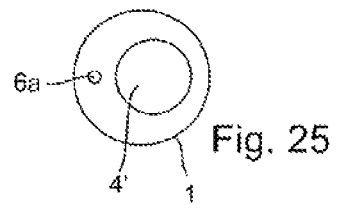
FIG. 25 is a view corresponding to FIG. 21 for the variant from FIG. 24.

FIGS. 24 and 25 illustrate a modification of the catheter variant from FIG. 23 to the effect that there is a central working channel 4' that is offset radially relative to the external shell of the catheter tube. FIGS. 24 and 25 show this offset towards the right. As a result, the solid material of the catheter tube surrounds the central working channel 4' both in the shaft portion 1 and also in the distal portion 2 with variable thickness, in the illustrated case with minimal thickness on the right side and on the left side with maximum thickness. In the right region of smaller thickness a ring segment-shaped part of the cross section of the distal section 2 is formed as the solid material stiffening zone 5₆; and the remaining solid material, including the region of larger thickness, forms a bending element 6'''.

A comparison of the FIGS. 24 and 25 with the FIGS. 20 to 23 reveals that this radial offset of the central working channel 4 makes possible a larger cross section of the working channel 4 and, thus, a larger useful volume at the same outside diameter of the catheter tube. In choosing a material that has a suitable flexural rigidity, the stiffening element solid material zone 5₆ in the region of less solid material thickness is adequate enough to provide the mandatory flexural rigidity of the distal portion 2, so that, as shown, just a ring segment extent of significantly less than 90° can be adequate enough for the stiffening element solid material zone 5₆. Even in the exemplary embodiment from FIGS. 24 and 25 the distal portion 2 can be easily manufactured by means of an extrusion process using two materials of different flexural rigidity.

Figure 26:
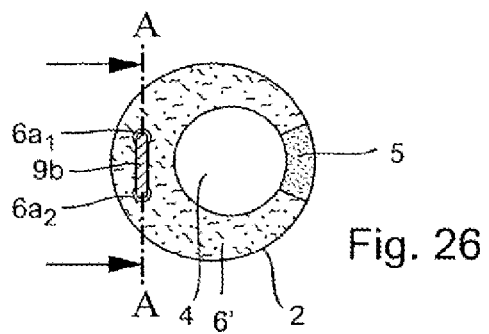
FIG. 26 is a view corresponding to FIG. 24 for a variant with a looped back tension wire.
Figure 27:
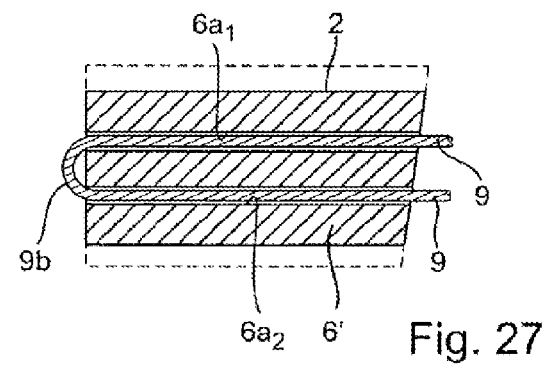
FIG. 27 is a longitudinal sectional view along a line A-A from FIG. 26.
Figure 28:
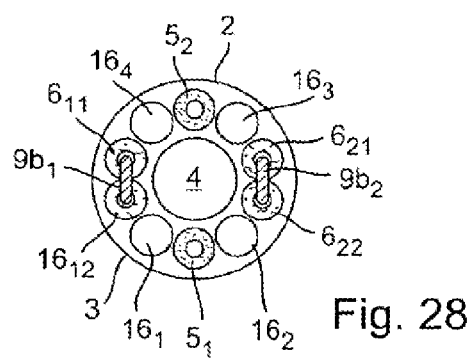
FIG. 28 is a view corresponding to FIG. 12 for a variant with looped back tension wires.

FIGS. 26 to 28 show catheter variants, in which a tension wire that is looped back through two hollow channels acts as the bending control element, as a result of which there is no need for the distal end of the tension wire to be fastened separately at the distal portion. In addition, FIGS. 26 and 27 illustrate an exemplary embodiment, which is based on the catheter variant from FIGS. 24 and 25 and is modified to the effect that, instead of the one hollow channel 6a, two adjacent hollow channels 6a₁, 6a₂ are incorporated into the bending element solid material zone 6''' of the solid material of the distal portion 2 and correspondingly into the solid material of the shaft portion. A one piece tension wire 9 extends through the one hollow channel—for example, the hollow channel 6a₁—as far as to the distal end of the distal portion 2 and is fed back from there, forming a corresponding return bend 9b through the other hollow channel—for example, the hollow channel 6a₂—as far as to the proximal end of the catheter tube.

In order to bend the distal portion 2, the two proximal ends of the tension wire 9, which is looped back through the two adjacent hollow channels 6a₁, 6a₂, are pulled synchronously. The return bend 9b of the tension wire 9 transfers the pulling force to the bending element solid material zone 6''' of the distal portion 2, as a result of which the desired bending of said distal portion is produced. A separate fastening of the tension wire at the distal portion 2 can be dispensed with; and there is also no need to design a distal tension wire end in a special way, as, for example, in the case of the tension wire head piece 9a in the catheter instrument according to FIGS. 4 to 6.

As a matter of fact, the use of such a tension wire, which is looped back through two adjacent hollow channels, is also possible for all of the other catheter variants. To this end FIG. 28 shows a catheter variant, which is based on the exemplary embodiment according to FIG. 12 and, as a modification, includes the measure that, instead of the bending element rod $6_1$, $6_2$, the respective bending element has not only the associated tension wire, but also two adjacent bending element rods $6_{11}$, $6_{12}$ or $6_{21}$, $6_{22}$ with one tension wire passage-hollow channel each. In this case a one piece tension wire $9_1$, $9_2$ is looped back through the two hollow channels of the two adjacent bending element rods $6_{11}$, $6_{12}$ or $6_{21}$, $6_{22}$ in the manner described above with reference to FIGS. 26 and 27. The deflection bend $9b_1$, $9b_2$ of each of these two looped through tension wires $9_1$, $9_2$ forms in turn the respective means for transmitting the force from the respective looped through tension wire $9_1$, $9_2$ to the two associated bending element rods $6_{11}$, $6_{12}$ or $6_{21}$, $6_{22}$.

The use of one or more looped through tension wires, as explained above with respect to the exemplary embodiments in FIGS. 26 to 28, allows the openings of the tension wire passage to be chosen smaller than in the case of a tension wire that is guided only as far as the distal end and then fastened there, because the pulling force is divided between the two synchronously operated parts of the tension wire. The deflection bend provides for a form-locking connection between the tension wire and the associated bending element(s), so that there is no need to provide for an additional fastening of the tension wire. The elimination of a distal fastening of the tension wire also eliminates the need to make sure that this fastening is adequately secured.

The above explanations of the advantageous exemplary embodiments clearly show that the invention provides a medical catheter instrument with a distal portion that can be bent, as desired, in an active and controlled manner or can be adjusted in its bending position in a very advantageous way. The bending motion is controlled preferably by means of tension wires of the type that are well known from the prior art for this purpose, for example by means of tension wires made of a solid wire material, a strip material or a plastic fiber material. If non-metallic or non-magnetic materials are used in the distal portion, then the catheter instrument, which can be bent in a controlled manner, also lends itself well, inter alia, to use during examinations with magnet resonance imaging processes. Doping the individual components of the distal portion with X-ray visible materials may enhance, if desired, the X-ray visibility of the catheter instrument. If magnet resonance imaging is used, then the visibility can also be enhanced with coatings or dopings that are visible under magnetic resonance imaging. The distal portion of the catheter instrument according to the invention can be controlled both actively in its bending movement and also elastically in the passive state, features that eliminate tissue injuries.

The invention claimed is:

1. A medical catheter instrument, comprising:
    a shaft portion;
    a distal portion bendable in a controlled manner in at least one direction relative to the shaft portion;
    at least one control element that extends in an axially moveable manner through the shaft portion to the distal portion, wherein axial movement of the at least one control element controls a corresponding bending movement of the distal portion; and
    at least one bending assembly comprising at least one elongated, elastically flexible stiffening element and at least one elongated, flexible and axially length-variable bending element, wherein:
        the at least one elongated, elastically flexible stiffening element and the at least one elongated, flexible and axially length-variable bending element are both provided in at least one axial subregion of the distal portion and extend within the distal portion with an axial main component,
        the at least one elongated, elastically flexible stiffening element forms a bending movement restoring element, which has a higher flexural rigidity than the at least one elongated, flexible and axially length-variable bending element,
        the at least one elongated, flexible and axially length-variable bending element coupled to the at least one control element and forms a part of the control element, and
        the at least one elongated, elastically flexible stiffening element extends from the distal portion into the shaft portion.

2. The catheter instrument according to claim 1, wherein the at least one control element comprises a tension wire, and further wherein the at least one elongated, flexible and axially length-variable bending element has a hollow channel, through which the tension wire is guided, the tension wire being coupled to a distal end region of the at least one elongated, flexible and axially length-variable bending element.

3. The catheter instrument according to claim 2, wherein the at least one elongated, flexible and axially length-variable bending element has two hollow channels, through which the tension wire is guided in one piece so as to form a return bend at the distal end region of the at least one elongated, flexible and axially length-variable bending element.

4. The catheter instrument according to claim 1, wherein the at least one elongated, flexible and axially length-variable bending element comprises one of an elastically compressible helical spring or hollow rod element and an elastically compressible solid material zone of the distal portion.

5. The catheter instrument according to claim 1, wherein the at least one elongated, elastically flexible stiffening element comprises one of an elastically tensible helical spring element or rod element and an elastically tensible solid material zone of the distal portion.

6. The catheter instrument according to claim 1, wherein the at least one elongated, elastically flexible stiffening element and the at least one elongated, flexible and axially length-variable bending element are arranged opposite each other relative to a longitudinally central axis of the distal portion.

7. The catheter instrument according to claim 1, wherein the at least one bending assembly comprises:
    at least two elongated, flexible and axially length-variable bending elements arranged opposite each other in a plane of the bending movement; and
    at least two elongated, elastically flexible stiffening elements arranged side by side in a plane transversely to the plane of the bending movement.

8. The catheter instrument according to claim 1, wherein:
    the distal portion is one of made of a solid material and made of two coaxial tubular elements; and
    the at least one bending assembly is provided in the solid material or in an annular space between the coaxial tubular elements.

9. The catheter instrument according to claim 1, wherein the distal portion has at least one of a central axial working channel and one or more off-centered axial working channels.

10. The catheter instrument according to claim 9, wherein:
    the distal portion is made of a solid material, which surrounds the central axial working channel with a non-uniform thickness; and
    the solid material's region of lesser thickness has an elastically tensible solid material zone as the at least one elongated, elastically flexible stiffening element.

11. The catheter instrument according to claim 10, wherein the solid material contains an elastically compressible zone, which comprises a region of greater thickness of the solid material, as the at least one elongated, flexible and axially length-variable bending element.

12. The catheter instrument according to claim 1, wherein:
a plurality of bending assemblies, each of which has at least one elongated, elastically flexible stiffening element and the at least one elongated, flexible and axially length-variable bending element, are provided in different axial subregions of the distal portion; and
at least a first and a second bending assembly have bending movement planes that do not extend parallel to each other.

13. The catheter instrument according to claim 12, wherein:
the distal portion comprises at least one light guide element and, coupled thereto, a luminous ring; and
the light guide element is accommodated in an axially extending manner in a working channel of the distal portion.

14. The catheter instrument according to claim 13, wherein:
the distal portion comprises a distal end piece, which is moveable in an axially elastic manner and which is connected to at least one guide pin, the guide pin being moveable in an axially elastic manner in an axial hollow channel of the distal portion.

15. The catheter instrument according to claim 1, wherein:
the distal portion comprises at least one light guide element and, coupled thereto, a luminous ring; and
the light guide element is accommodated in an axially extending manner in a working channel of the distal portion.

16. The catheter instrument according to claim 1, wherein:
the distal portion comprises a distal end piece, which is moveable in an axially elastic manner and which is connected to at least one guide pin, the guide pin being moveable in an axially elastic manner in an axial hollow channel of the distal portion.

17. A medical catheter instrument, comprising:
a shaft portion;
a distal portion bendable in a controlled manner in at least one direction relative to the shaft portion;
at least one control element that extends in an axially moveable manner through the shaft portion to the distal portion, wherein axial movement of the at least one control element controls a corresponding bending movement of the distal portion; and
at least one bending assembly comprising at least one elongated, elastically flexible stiffening element and at least one elongated, flexible and axially length-variable bending element, wherein:
the at least one elongated, elastically flexible stiffening element and the at least one elongated, flexible and axially length-variable bending element are both provided in at least one axial subregion of the distal portion and extend therein with an axial main component,
the at least one elongated, elastically flexible stiffening element forms a bending movement restoring element, which has a higher flexural rigidity than the at least one elongated, flexible and axially length-variable bending element,
the at least one elongated, flexible and axially length-variable bending element is coupled to the at least one control element and forms a part of the control element, and
the distal portion comprises a distal end piece, which is moveable in an axially elastic manner and which is connected to at least one guide pin, the guide pin being moveable in an axially elastic manner in an axial hollow channel of the distal portion.

18. A medical catheter instrument, comprising:
a shaft portion;
a distal portion bendable in a controlled manner in at least one direction relative to the shaft portion;
at least one control element that extends in an axially moveable manner through the shaft portion to the distal portion, wherein axial movement of the at least one control element controls a corresponding bending movement of the distal portion, and wherein the at least one control element comprises a tension wire; and
at least one bending assembly comprising at least one elongated, elastically flexible stiffening element and at least one elongated, flexible and axially length-variable bending element, wherein:
the at least one elongated, elastically flexible stiffening element and the at least one elongated, flexible and axially length-variable bending element are both provided in at least one axial subregion of the distal portion and extend within the distal portion with an axial main component,
the at least one elongated, elastically flexible stiffening element forms a bending movement restoring element, which has a higher flexural rigidity than the at least one elongated, flexible and axially length-variable bending element,
the at least one elongated, flexible and axially length-variable bending element is coupled to the at least one control element and forms a part of the control element,
the at least one elongated, elastically flexible stiffening element extends from the distal portion into the shaft portion, and
the at least one elongated, flexible and axially length-variable bending element has two hollow channels, through which the tension wire is guided in one piece so as to form a return bend at a distal end region of the at least one elongated, flexible and axially length-variable bending element.

* * * * *